(12) United States Patent
Kondo et al.

(10) Patent No.: US 8,742,178 B2
(45) Date of Patent: Jun. 3, 2014

(54) PROCESS FOR SYNTHESIS OF ACROLEIN

(75) Inventors: Takeyuki Kondo, Hitachi (JP);
Hiroyuki Ito, Tokyo (JP); Yasunari Sase, Tokyo (JP); Toshiaki Matsuo, Mito (JP); Kenichiro Oka, Mito (JP); Masayuki Kamikawa, Hitachinaka (JP); Masashi Tanto, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 13/577,680

(22) PCT Filed: Feb. 9, 2010

(86) PCT No.: PCT/JP2010/051846
§ 371 (c)(1),
(2), (4) Date: Aug. 8, 2012

(87) PCT Pub. No.: WO2011/099112
PCT Pub. Date: Aug. 18, 2011

(65) Prior Publication Data
US 2012/0310016 A1 Dec. 6, 2012

(51) Int. Cl.
*C07C 45/00* (2006.01)
(52) U.S. Cl.
USPC .......................... 568/484; 568/486
(58) Field of Classification Search
USPC .......................... 568/461, 484, 486
See application file for complete search history.

(56) References Cited

U.S. PATENT DOCUMENTS

2009/0068440 A1 3/2009 Bub et al.
2011/0319667 A1 12/2011 Kondo et al.

FOREIGN PATENT DOCUMENTS

| JP | 2007-137785 | 6/2007 |
|---|---|---|
| JP | 2008-88149 | 4/2008 |
| JP | 2008-546660 | 12/2008 |
| JP | 2009-132663 | 6/2009 |
| JP | 2010-13367 | 1/2010 |
| JP | 2010-184897 | 8/2010 |

OTHER PUBLICATIONS

Production, applications and economic efficiency of 1,3-PDO and PTT, CMC Publishing Co., Ltd., Planet Division, Aug. 2000.
Masaru Watanabe et al., Acrolein synthesis from glycerol in hot-compressed water, Bioresource Technology 98 (2007) 1285-1290.
Enhancement in reaction yield in synthesis of acrolein from high concentration glycerol using supercritical water, 74th Annual Meeting (2009) The Society of Chemical Engineers, Japan J108.
Michael Jerry Antal, Jr. et al., Heterolysis and Homolysis in Supercritical Water, American Chemical Society, Division of Fuel Chemistry, 1995 30 (3), pp. 78-87.
Sundaresh Ramayya et al., Acid-catalysed dehydration of alcohols in supercritical water, Fuel, Oct. 1987, pp. 1364-1371, vol. 66.

*Primary Examiner* — Sikarl Witherspoon
(74) *Attorney, Agent, or Firm* — Antonelli, Terry, Stout & Kraus, LLP.

(57) ABSTRACT

An object of the present invention is to provide a technology which can suppress the blockage and abrasion of pipes and devices caused by the production of by-products and stably synthesize acrolein at a high yield, under a condition in which energy efficiency is improved by an elevated concentration of glycerol in a reaction liquid, in a process for synthesis of acrolein by reacting supercritical water and an acid with glycerol. An embodiment of the present invention includes: setting a concentration of glycerol in the reaction liquid at 30% by weight or lower; also cooling the reaction liquid to a temperature between a temperature (300° C. or lower) at which the reaction stops and a temperature (100° C. or higher) at which tar contained in the reaction liquid can keep a state in which its viscosity is sufficiently low; then separating and removing carbon particles from the reaction liquid; subsequently cooling the reaction liquid to a temperature which is a boiling point of water or lower and at which the tar component in the reaction liquid does not adhere to devices; and then decompressing the cooled reaction liquid.

8 Claims, 7 Drawing Sheets

Dependency of the maximum reaction yield on $[H^+]^2/[G]$

Fig. 4

Dependency of reaction time in which yield becomes maximal, on glycerol concentration

Fig. 5

Dependency of side reaction rate on temperature

Fig. 6

Dependency of tar viscosity at 35 MPa on temperature

Fig. 7

Particle size distribution of carbon particle

Fig. 8

Dependency of the maximum reaction yield on glycerol concentration

Fig. 9

Dependency of continuous operation time on filtration temperature and pore diameter of filter

Fig. 10

Dependency of composition of cake on filtration temperature

Fig. 11

PROCESS FOR SYNTHESIS OF ACROLEIN

TECHNICAL FIELD

The present invention relates to a process for synthesis of an organic material by using supercritical water, and in more detail, relates to a process for synthesis of acrolein which is a raw material of 1,3-propanediol, from glycerol in the presence of protons.

BACKGROUND ART

Because 1,3-propanediol (1,3-PDO) is a raw material of a polyester fiber of high quality, which includes polytrimethylene terephthalate (PTT), the demand is increasing in recent years. As one process for synthesis of 1,3-propanediol, there is an acrolein hydration and hydrogenation process shown in Non-Patent Literature 1. This process is a production method involving subjecting acrolein which has been obtained by oxidizing propylene that is a crude oil material with air in the presence of a catalyst, to a hydration/hydrogenation reaction, and is established as an industrial production method. However, it has been desired in recent years to develop a process for synthesis of 1,3-propanediol from a biological raw material, on the background of a remarkable rise of a crude oil price.

A process for synthesis of 1,3-propanediol from a biological raw material with a chemical synthesis process is not reported, but technologies for synthesizing acrolein which is a precursor exist, and one of the technologies is described in Non-Patent Literature 2. This process is a process for synthesis of acrolein by using glycerol which is a biological raw material as a starting material, and using a supercritical water of 400° C. at 35 MPa. The process has a feature in the point that a proton originating from a trace quantity of sulfuric acid added into the supercritical water has an effect of increasing a generation amount of active hydrogen ions which trigger the dehydration reaction of glycerol in supercritical water, and functions as a co-catalyst for accelerating the progress of the reaction. However, in Non-Patent Literature 2, the concentration of glycerol in a raw material is as extremely low as about 1%, but on the other hand, much energy is consumed for raising the temperature and pressure of water when producing the supercritical water. Accordingly, there has been a problem that the utilization efficiency for energy is extremely poor in consideration of commercial production.

In contrast to this, in Non-Patent Literature 3, optimum conditions on a reaction time and the concentration of sulfuric acid which is a co-catalyst have been derived, a reaction experiment has been carried out under a condition in which the concentration of glycerol has been increased to 15% by weight, and a reaction yield exceeding 70% has been attained. Thereby, energy efficiency is improved, but in order to structure a process having market competitiveness, the running cost needs to be reduced by increasing the concentration of glycerol to the limit. On the other hand, as the concentration of glycerol increases, the amount of produced reaction by-products such as tar and a carbon particle increases. Then, the by-product adheres to a valve element and a valve seat of a valve, thereby the valve element and the valve seat are abraded, the operation range of the valve element is restricted, and it may become difficult to precisely control the pressure. If the operation is further continued, the by-product causes blockage in narrow portions such as a pipe, the valve and a filter, and it may become difficult to operate the plant. The reason is because the carbon particles coagulate and grow due to the adhesiveness of tar. In Non-Patent Literature 3, such problems are not studied.

The technology in Patent Literature 1 relates to a method for producing acrolein, which includes at least steps of: (a) obtaining an aqueous acrolein reaction phase at least one part of which is in a supercritical region, by supplying an aqueous glycerol phase to an acrolein reaction region; (b) removing acrolein from the above described acrolein reaction phase, and obtaining an acrolein phase and an acrolein reaction phase in which the concentration has been reduced; and (c) resupplying at least one part of the acrolein reaction phase in which the concentration has been reduced, to the acrolein reaction region. Patent Literature 1 discloses that the acrolein reaction region preferably contains a dehydration catalyst other than water, that the dehydration catalyst is a compound except water, which has acidity and also acts as a strong acid in a region near the supercritical region or in the supercritical region, that the glycerol phase contains less than 10% by weight of, particularly preferably less than 8% by weight of and most preferably less than 6% by weight of glycerol with respect to the total amount of the glycerol phase, that the least amount of glycerol in the glycerol phase is preferably 0.01% by weight, particularly preferably is 0.1% by weight and most preferably is 1% by weight, and the like. However, in the present Literature, the concentration less than 10% by weight of glycerol is a value in which a sufficient utilization efficiency of energy is not necessarily obtained, and measures against the tar and the carbon particle are not studied. Accordingly, the commercialization of the method is difficult.

The technology in Patent Literature 2 relates to a method for producing acroleins, which includes using a supercritical fluid or a subcritical fluid in a high-temperature and high-pressure state as a reaction solvent, and selectively synthesizing acroleins by one stage of a synthesis reaction from glycerols under the condition of using no catalyst or a trace quantity of a catalyst, in a process for synthesis of acroleins. Patent Literature 2 discloses to use a supercritical fluid or a subcritical fluid in a high-temperature and high-pressure state as a reaction solvent, to use water in a supercritical or subcritical state as the supercritical fluid or the subcritical fluid, to use an inorganic acid as a trace quantity of a catalyst, to use an aqueous solution in which a trace quantity of a catalyst has been added to an aqueous solution of glycerols, as a raw material, and to subject the aqueous solution to a reaction. However, under conditions with no catalyst, at a temperature of 350° C. or lower and with a pressure of 22 MPa or less in the present literature, an amount of generated active hydrogen ions (having catalysis action), which should act on glycerol, is small, and the reaction becomes extremely slow. For this reason, the influence of the conversion of a reactant to tar or carbon particles due to a thermal decomposition reaction which is a side reaction becomes large, and such problems are caused that the a yield of a raw material decreases and a blockage occurs in a pipe. The measures against the problems are not also studied.

The technology in Patent Literature 3 relates to a catalyst which is preferably used when acrolein or an aqueous solution of acrolein is produced by volatilizing an aqueous solution of glycerol and using a dehydration reaction in a gaseous phase using a solid catalyst, and to a method for producing acrolein using the catalyst. Patent Literature 3 describes that the glycerol of a raw material may contain also 0 to 95% by weight of an inactive condensable substance such as water, that a solvent or the like may also exist which is not involved in the reaction, and that the concentration of the glycerol of the raw material is preferably 5 to 100% by weight. However, in the present method, by-products such as tar and carbon particles are produced and if the by-products cover the interface of a catalyst, the reactivity is remarkably lowered. For this reason, catalyst regeneration treatment is frequently needed, a plant operation becomes complicated, and besides a catalyst performance is lowered by the aggregation of carried precious-metal particles along with a regeneration operation which is ordinarily heat treatment, which becomes a problem that is difficult to be solved.

CITATION LIST

Patent Literature

Patent Literature 1: JP translation of PCT International Application Publication No. 2008-546660 A
Patent Literature 2: JP Patent Application Publication No. 2009-132663 A
Patent Literature 3: JP Patent Application Publication No. 2008-88149 A Non Patent Literature Non Patent Literature 1: Production, applications and economic efficiency of 1,3-PDO and PTT, CMC Publishing Co., Ltd., Planet Division, August, 2000
Non Patent Literature 2: "Acrolein synthesis from glycerol in hot-compressed water, Bioresource Technology 98 (2007) 1285-1290"
Non Patent Literature 3: Enhancement of reaction yield in synthesis of acrolein from high concentration glycerol using supercritical water, 74th Annual Meeting (2009) The Society of Chemical Engineers, Japan J108

SUMMARY OF INVENTION

Technical Problem

An object of the present invention is to provide a technology which can suppress the blockage and abrasion of pipes and devices caused by the production of a by-product and stably synthesize acrolein at a high yield, under a condition in which energy efficiency is improved by an elevated concentration of glycerol in a reaction liquid, in a process for synthesis of acrolein by reacting supercritical water and an acid with glycerol.

Solution to Problem

In order to solve the above described problems, an embodiment of the present invention includes: setting the concentration of glycerol in a reaction liquid at 30% by weight or lower; also cooling the reaction liquid to a temperature between a temperature (300° C. or lower) at which the reaction stops and a temperature (200° C. or higher) at which tar contained in the reaction liquid can keep a state in which its viscosity is sufficiently low; then separating and removing carbon particles from the reaction liquid; subsequently cooling the reaction liquid to a temperature which is a boiling point of water or lower and at which the tar component in the reaction liquid does not adhere to devices; and then decompressing the cooled reaction liquid.

Another embodiment for enhancing the effect of the present invention includes setting a proton concentration [H⁺] (% by weight) in the reaction liquid, in a range expressed by [Formula 1] using a glycerol concentration [G] (mM), in the above described process for synthesis.

$$5 \times \sqrt{[G]} < [H^+] < 20 \times \sqrt{[G]}$$ [Formula 1]

Another embodiment for enhancing the effect of the present invention includes setting a reaction time t in a range expressed by [Formula 2] using the glycerol concentration [G] (mM) in the reaction liquid, in the process for synthesis.

$$\frac{3.75}{[G]} < t < \frac{1.5}{[G]}$$ [Formula 2]

Another embodiment for enhancing the effect of the present invention includes setting the pore diameter of a filter for separating and removing a solid component at 40 micrometers or less, in the process for synthesis.

Another embodiment for enhancing the effect of the present invention includes setting the concentration of glycerol at 15% by weight or higher, in the process for synthesis.

Advantageous Effects of Invention

According to the present invention, because the first cooling temperature is a temperature at which the reaction stops, a reaction time can be precisely controlled, and the amount of by-products to be produced can be reduced. Furthermore, because the first cooling temperature is a temperature at which a tar component in the reaction liquid can keep its low viscosity, only carbon particles in the by-product are efficiently separated by a filter having an appropriate pore diameter, and only the tar can pass through the filter. Thereby, the carbon particles can be prevented from coagulating, growing and strongly depositing on the filter, which originate in the adhesiveness of the tar, accordingly pipes can be prevented from causing a blockage, and a decompression valve in a subsequent stage also can be prevented from being abraded by the carbon particles.

DESCRIPTION OF EMBODIMENTS

Figure 8:
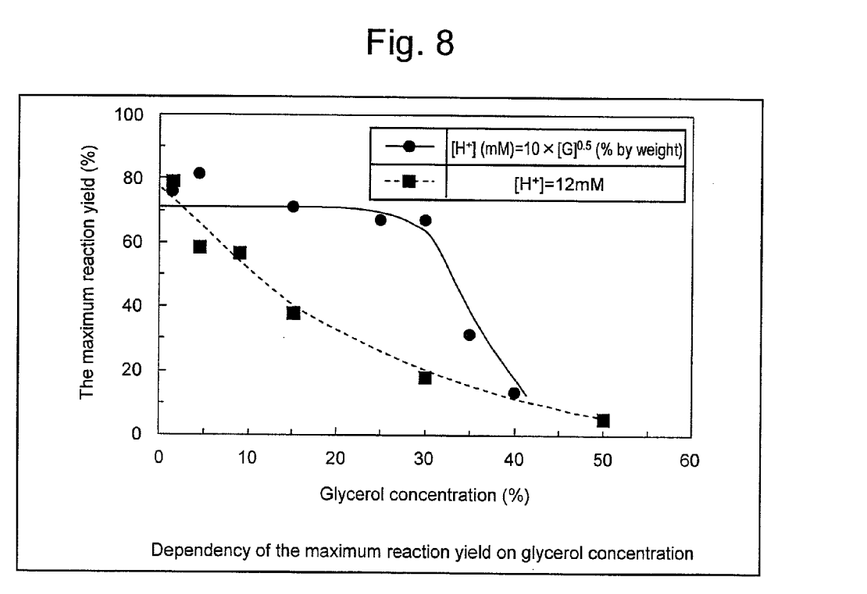
FIG. 8 is a view illustrating the dependency of the maximum reaction yield on glycerol concentration.

In an embodiment of the present invention, the concentration of glycerol in a reaction liquid is set at 30% by weight or lower. This concentration is illustrated in a path of a dehydration reaction of glycerol, which occurs when supercritical water has been used, in FIG. 1. When the concentration is set at 30% by weight or lower, the numbers (molar ratio) of coordinating water which constitutes a cluster with glycerol and of an acting water for generating an active hydrogen ion in a supercritical state are sufficient, an appropriate main reaction dominantly progresses (proton adds to secondary hydroxyl group of glycerol, and dehydration reaction progresses twice). Then, acrolein which is a target substance tends to be easily synthesized, and accordingly a reaction yield can be enhanced. On the other hand, when the concentration of glycerol is set at 30% by weight or higher, the ratio of water is relatively lowered, and the coordinating water and the acting water result in gradually becoming insufficient. In this case, a location to which an active hydrogen ion acts in a glycerol molecule changes (dehydration reaction in a primary hydroxyl group becomes dominant), and a substance except the target substance, such as formaldehyde and acetaldehyde, is produced. According, the yield of a raw material is lowered on the contrary (FIG. 8). This is the reason why the above described concentration of the glycerol is determined to be the upper limit.

Figure 5:
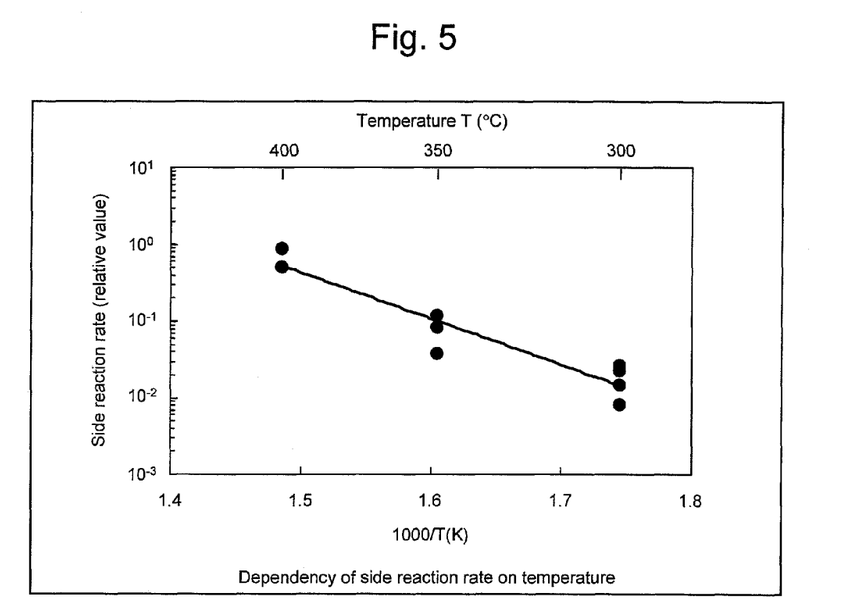
FIG. 5 is a view illustrating the dependency of a side reaction rate on temperature.
Figure 6:
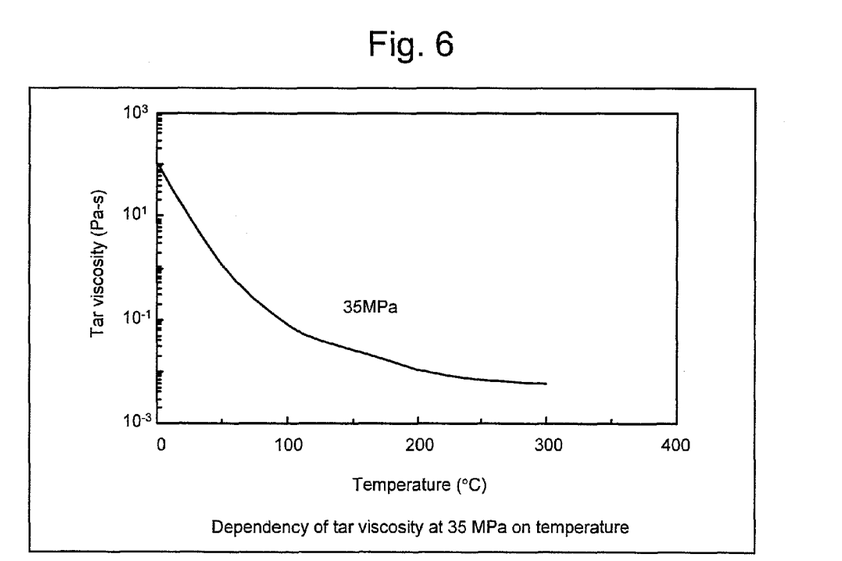
FIG. 6 is a view illustrating the dependency of tar viscosity at 35 MPa on temperature.

In addition, the supercritical water and the glycerol are subjected to the reaction at a predetermined temperature (350 to 450° C.) and a predetermined pressure (30 to 40 MPa) for a predetermined time (0.1 to 10 s), and then the reaction liquid is cooled. At this time, the cooling temperature is set at the temperature (300° C., and desirably 260° C.) or lower at which a main reaction and a side reaction (thermal decomposition) which generates the tar and the carbon particles can be sufficiently stopped. In this regard, FIG. 5 illustrates a correlation between the temperature and the reaction rate constant of the side reaction. As the reaction temperature is lowered by every 50° C., the reaction rate constant decreases approximately by one digit. Accordingly, when the reaction temperature is 400° C., for instance, by setting the cooling temperature at 300° C. or lower, the side reaction can be lowered by two digits or more. Furthermore, on the other hand, the cooling temperature must not be set at the temperature (200° C., and desirably 240° C.) or lower at which the tar contained in the reaction liquid can keep a state in which its viscosity is sufficiently low. This also originates in such a phenomenon that as the temperature is lowered, the viscosity of the tar sharply elevates, as is illustrated in FIG. 6. The viscosity of the tar is desirably in a range of $10^{-2}$ to $10^{-3}$ Pa·s or lower, in consideration of the viscosity of water.

Accordingly, the temperature of cooling after the reaction shall be 200 to 300° C., and desirably shall be 240 to 260° C. which is a region around the center value between the above temperatures. The reaction liquid needs to be instantly cooled in consideration of the shortness of the reaction time. Then, the cooling method is desirably a method of directly mixing the cooling water with the reaction liquid, though the cooling method may be an indirect method of cooling the reaction liquid by a jacket of cooling water on the outside of a reaction pipe. Furthermore, a filter is provided in a stage subsequent to the cooling (first cooling) stage of the reaction liquid, and a solid material is removed. For information, the above described temperature range is set because the blockage of pipes originates in that a tar component mainly existing on the surface of the carbon particles generates a coagulation effect and consequently produces large depositable particles. When the viscosity of tar is kept low, the carbon particles are trapped by the filter. On the other hand, the tar flows to the stage subsequent to the filter, and accordingly the production of large and strongly depositable particles due to the above described coagulation effect can be suppressed.

Figure 2:
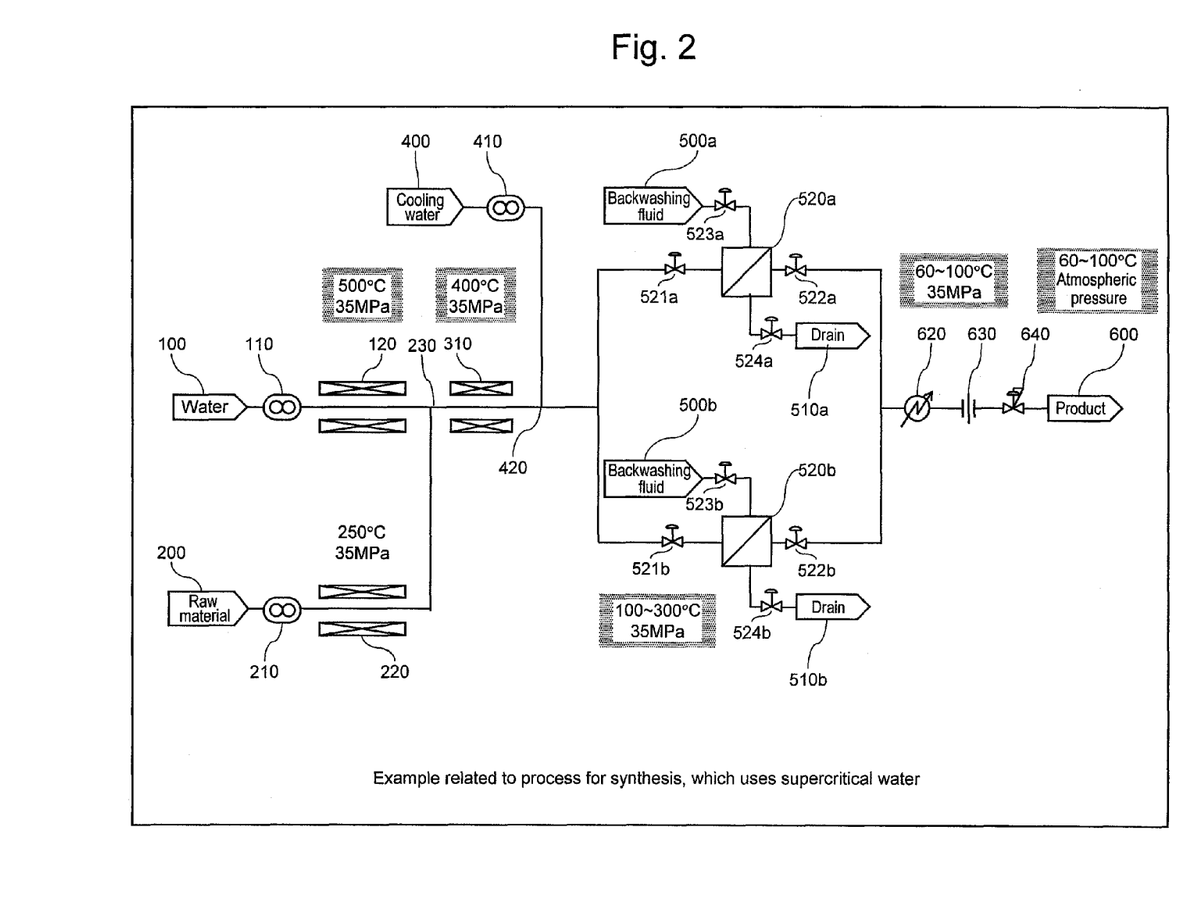
FIG. 2 is a view illustrating an example related to a process for synthesis which uses supercritical water.

As for the filter system, in order that the continuous operation of a plant is not hindered, it is desirable to install a plurality of stages of the filters provided with a backwashing apparatus in parallel so that the filters can be operated while being switched (FIG. 2). After the reaction liquid has been subjected to the first cooling and the carbon particles are separated and removed from the reaction liquid, the resultant reaction liquid is cooled (second cooling) to a temperature which is a boiling point of water or lower and at which the tar component in the reaction liquid does not adhere to devices such as a decompression valve in stages subsequent to the filter. The cooling temperature is 50 to 200° C., and desirably is 50 to 100° C. When the cooling temperature is set at 100° C. or lower, sudden boiling in a stage subsequent to the decompression valve can be prevented, which is more desirable. After that, the pressure is lowered, and the reaction liquid is further cooled, as needed.

Another embodiment for enhancing the effect of the present invention includes setting a proton concentration [H$^+$] (% by weight) in the reaction liquid, which originates in the addition of an acid (co-catalyst), in a range expressed by [Formula 1] using a glycerol concentration [G] (mM), in the process for synthesis.

$$5 \times \sqrt{[G]} < [H^+] < 20 \times \sqrt{[G]} \quad \text{[Formula 1]}$$

Figure 3:
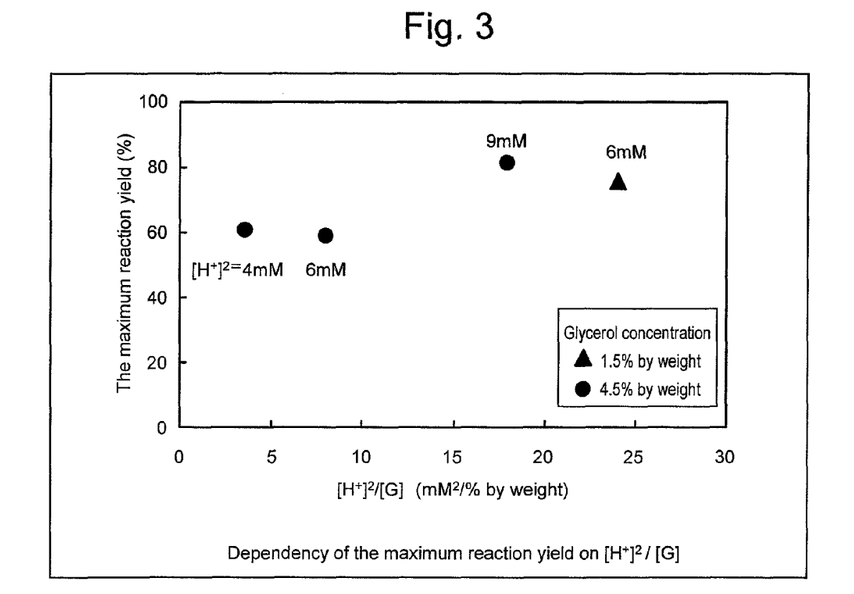
FIG. 3 is a view illustrating the dependency of the maximum reaction yield on $[H^+]^2/[G]$.

For information, [Formula 1] has been obtained from the result (FIG. 3) of an experiment which has been conducted by the present inventors for investigating the correlation between the glycerol concentration and the acid concentration, and the maximum reaction yield obtained at that time, and shows that a maximum reaction yield similar to the raw material yield to be obtained on a condition of a certain glycerol concentration is obtained in another glycerol concentration as well, by controlling $[H^+]^2/[G]$ to an acid concentration within a range expressed by [Formula 1].

Another embodiment for enhancing the effect of the present invention includes setting a reaction time t in a range expressed by [Formula 2] using the glycerol concentration [G] (mM) in the reaction liquid, in the process for synthesis.

$$\frac{3.75}{[G]} < t < \frac{1.5}{[G]} \quad \text{[Formula 2]}$$

For information, [Formula 2] has been obtained from the result (FIG. 4) of an experiment which has been conducted by the present inventors for investigating the correlation between an appropriate reaction time and a glycerol concentration by which the maximum reaction yield is obtained, and shows that when the glycerol concentration is determined, the raw material yield becomes maximal in the reaction time contained in a range expressed by [Formula 2].

Figure 7:
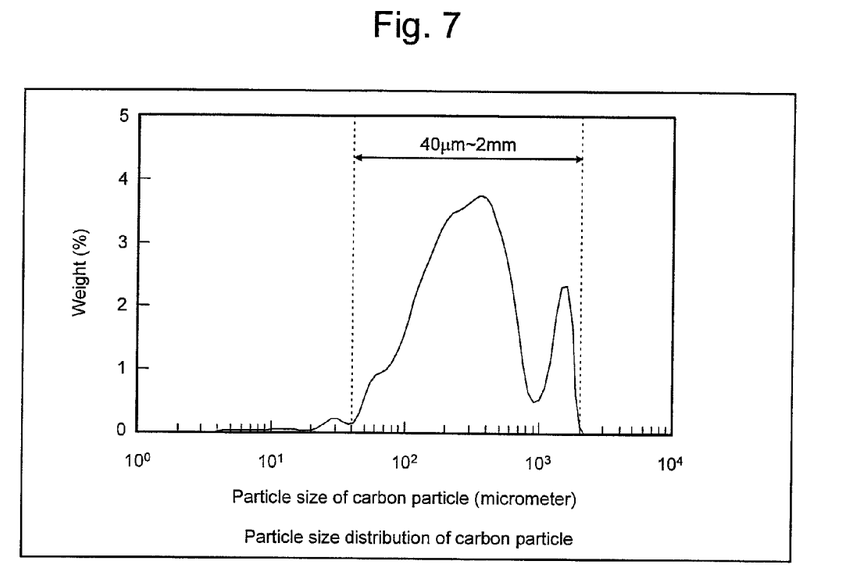
FIG. 7 is a view illustrating the particle size distribution of carbon particles.

Another embodiment for enhancing the effect of the present invention includes setting the pore diameter of a filter for separating and removing a solid component at 40 micrometers or less, in the process for synthesis. This is because as a result of analysis on the particle size distribution of carbon particles which are produced by a reaction of the supercritical water and the glycerol, the main portion is specified to be in a range of approximately 40 micrometers to 2 mm, as is illustrated in FIG. 7. However, when the pore diameter of the filter is set to be excessively small, a differential pressure remarkably rises, and accordingly the pore diameter is desirably set at least 4 micrometers or more, which is not confirmed in the particle size distribution of FIG. 7.

Another embodiment for enhancing the effect of the present invention includes setting the concentration of glycerol at 15% by weight or higher, in the process for synthesis. This originates in that acrolein cannot be economically produced if the use efficiency of energy is not a value corresponding to 15% by weight or higher of the glycerol concentration, in consideration of a cost necessary for producing the supercritical water.

A flow of mixing a raw material with supercritical water to start a reaction, separating and removing a by-product and then collecting a reaction liquid will be described below with reference to the drawings.

Figure 1:
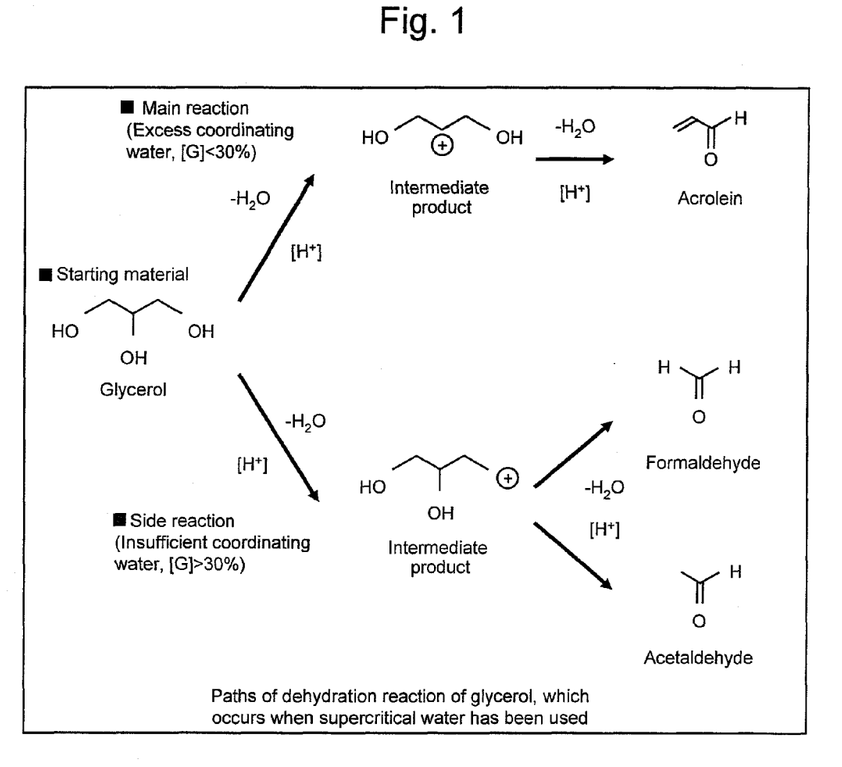
FIG. 1 is a view illustrating paths of a dehydration reaction of glycerol, which occurs when supercritical water has been used.

FIG. 2 illustrates one example of an apparatus for synthesizing acrolein according to the present invention. Firstly, water is sent at 35 MPa by a high-pressure pump (110) for supercritical water, and the temperature is raised to 500° C. by a supercritical water preheater (120). In addition, a raw material formed of glycerol and dilute sulfuric acid is sent at 35 MPa by a high-pressure pump (210) for a raw material, and the temperature is raised to 250° C. by a raw material preheater (220). Both of the water and the raw material are mixed with each other at a joining point (230), and are instantly controlled to 400° C. and 35 MPa. Then, the reaction starts. Here, in the present embodiment, because the glycerol concentration immediately after having been joined is controlled to 30% by weight or lower, at least 8 or more water molecules result in coordinating to the periphery of the glycerol molecule. Thereby, a main reaction progresses in which a proton adds to a secondary hydroxyl group of the glycerol as is illustrated in FIG. 1, and accordingly a high concentration of glycerol is obtained while a high reaction yield is maintained. Thereby, a cost for synthesizing the acrolein can be reduced. At the same time, the main reaction becomes dominant, accordingly the amount of by-products to be produced can be reduced, and pipes can be prevented from causing a blockage.

For information, 30% by weight, which is the upper limit of the glycerol concentration, is calculated in the following way. Specifically, the glycerol molecule with a molecular weight of 92 has three hydroxyl groups, and it is anticipated that six water molecules form coordinate bonds with hydroxyl groups to form a cluster centering on the glycerol molecule. Accordingly, in addition to the six coordinating water molecules, two or more water molecules which develop reaction activity by a supercritical condition are necessary for the reaction. This is because the acrolein is produced through two dehydration reactions which use the proton as a catalyst. From this anticipation, it is considered that when a molar ratio M of water to glycerol becomes (6+2)/1=8 or less, an effect of the supercritical water reaction decreases, and the yield possibly decreases compared to expectation. Now, suppose that an initial glycerol concentration is represented by [G] (% by weight), and molar concentrations (mol/m³) of the glycerol and the water are expressed by ([G]/100)×1000/92, and (100−[G])/100×1000/18, respectively. Accordingly, the molar ratio M of the glycerol and the water is expressed by the following formula.

$$M = \frac{\left(\frac{100-[G]}{100}\right)\left(\frac{1000}{18}\right)}{\left(\frac{[G]}{100}\right)\left(\frac{1000}{92}\right)} \quad \text{[Formula 3]}$$

The formula is arranged to provide the following formula.

$$[G]_0 = \frac{4600}{(9M+46)} \quad \text{[Formula 4]}$$

(17) When M=8 is substituted into the formula, [G]0 becomes 38% by weight. From this result, when the supercritical water contributes to the reaction 100% effectively, the upper limit value of the glycerol concentration at which the main reaction dominantly progresses becomes 38% by weight, but actually water which is not effectively used exists, and accordingly it is considered that the glycerol concentration needs to be set at 30% by weight or lower.

For information, it is desirable to control the glycerol concentration to 15% by weight or higher, in order to give cost competitiveness to a process for synthesis of the acrolein from a crude oil material.

Figure 4:
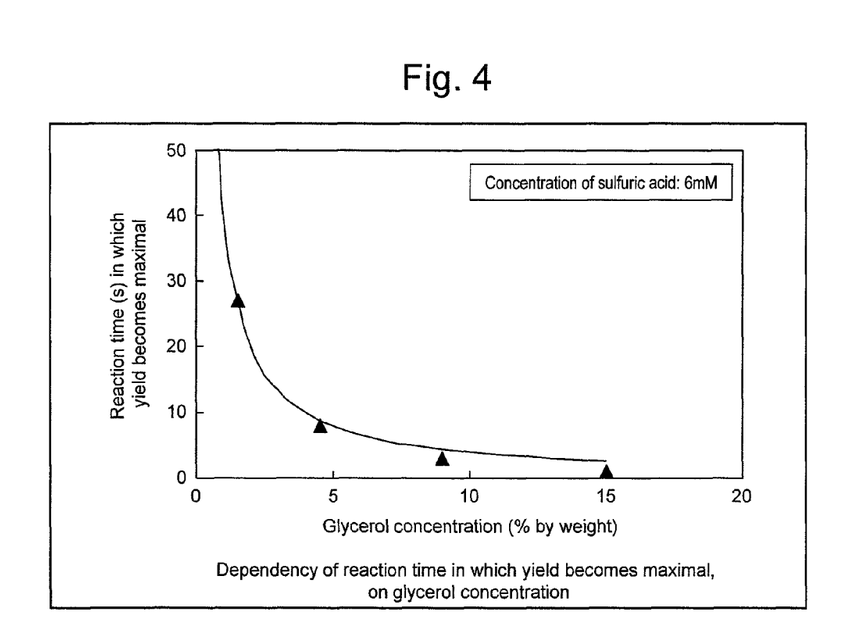
FIG. 4 is a view illustrating the dependency of a reaction time in which the yield becomes maximal on glycerol concentration.

In addition, because the proton concentration in the reaction liquid is set in a range of [Formula 2], the reaction yield can be enhanced. The enhancement of a reaction yield leads to the reduction of the amount of the by-products to be produced, and accordingly is extremely effective for preventing the blockage of pipes and the abrasion of devices. FIG. 4 illustrates a result obtained by arranging the maximum reaction yields with respect to $[H^+]^2/[G]$, which have been obtained from a reaction experiment that has set the glycerol concentration and the sulfuric acid concentration as parameters and has been conducted by the present inventors. It is understood that the reaction yields are low which have been obtained under a condition in which $[H^+]^2/[G]$ is small, in other words, there is a shortage of protons, but the reaction yields of 70% or higher are obtained under a condition in which there are sufficiently many protons.

Next, in order to stop the reaction after the optimal reaction time has passed, a cooling water is sent to a joining point (420) by using a high-pressure pump (410) for cooling water in FIG. 2, and is directly mixed with the reaction liquid thereby to stop the reaction. FIG. 6 illustrates the dependency of a reaction rate on temperature. In order to stop the reaction, the reaction rate needs to be lowered approximately by two digits. Because of this, the temperature of the reaction liquid needs to be lowered from 400° C. to 300° C. or lower, by the direct mixing of the cooling water. Incidentally, the optimal reaction time for the present reaction is an order of seconds, and in an actual apparatus, the inner diameter of a reaction pipe becomes as thick as approximately 10 cm. Accordingly, a method of directly mixing the cooling water enhances the controllability of the reaction time in comparison with a method of indirectly cooling the reaction liquid by using a double tube cooler. For this reason, the directly mixing method is extremely effective in reducing the amount of by-products to be produced.

The reaction liquid in which the reaction has stopped is sent to filters (520a and 520b) in the subsequent stage, carbon particles are separated there from tar, only the carbon particles are captured by the filters, and the tar are passed through the filters in a state of having kept its high viscosity. Thereby, the blockage of the pipes due to the coagulation of the tar and the carbon particles is prevented. FIG. 7 illustrates the dependency of the viscosity of the tar at 35 MPa on temperature. At this time, when the viscosity of the tar is controlled to 0.1 Pa·s or lower, the tar causes clogging in the filter, and accordingly a reaction-stopping temperature needs to be set at 100° C. or higher. From the above described results, the temperature of the reaction liquid after the cooling water has been mixed with the reaction liquid needs to be controlled to 100° C. to 300° C., and desirably needs to be controlled to 250° C. A method of cooling the reaction liquid, then filtering the cooled reaction liquid and removing impurities therefrom is extremely effective also for lowering a corrosion rate of the filter. FIG. 8 illustrates the particle size distribution of carbon particles, which has been used by the present inventors. Because the carbon particles are distributed in a range of 40 micrometers to 2 mm, the separating and removing performance for the carbon particles can be enhanced by setting the pore diameter of the filter at 40 micrometers or less.

For information, if two or more systems are prepared for the separating and removing filter for the carbon particles, an operation of discharging a cake of the carbon particles by back washing can be alternately conducted. Thereby, the whole plant does not need to be stopped, and accordingly it becomes possible to enhance a continuous operability, to reduce a heat loss which originates in starting the operation of the plant, and to reduce an operating cost.

The reaction liquid from which the carbon particles have been removed is cooled to 60 to 100° C. by a second cooler (620), then the pressure is lowered to an atmospheric pressure by an orifice (630) and a pressure control valve (640), and the reaction liquid is sent to a distillation apparatus of acrolein in the subsequent stage. Here, there are two reasons why the reaction liquid is cooled to 60 to 100° C. One reason is to prevent the volume of water from expanding when the pressure is opened down to the atmospheric pressure, and to secure the stability and safety of the process. Another reason is to enhance heating efficiency in a distillation step because the distillation temperature of the acrolein is 60 to 100° C., and to reduce the operation cost. In addition, there is no problem in controlling the pressure with only the pressure control valve (640), but it is desirable to use the orifice (630) together for the purpose of reducing a load to be applied to a valve body.

According to the present embodiment, the first cooling temperature is a temperature at which the reaction stops, accordingly a reaction time can be precisely controlled, and the amount of by-products to be produced can be reduced. Furthermore, because the first cooling temperature is a temperature at which a tar component in the reaction liquid can keep its low viscosity, only carbon particles in the by-products are efficiently separated by a filter having an appropriate pore diameter, and only the tar can pass through the filter. Thereby, the carbon particles can be prevented from coagulating, growing and strongly depositing on the filter, which originate in the adhesiveness of the tar, accordingly pipes can be prevented from causing a blockage, and a decompression valve in a subsequent stage also can be prevented from being abraded by the carbon particles. In addition, because an increasing rate of the differential pressure of the filter can be controlled to the minimum rate while the carbon particles are captured by the filter, the frequency of the back washing of the filter becomes few, which can contribute to the stable operation of the plant. At this time, the plant can be actually operated in an appropriate concentration of glycerol, in an appropriate acid concentration and for an appropriate reaction time by using [Formula 1] and [Formula 2], and accordingly the plant can be operated which has a high reaction yield and a high use efficiency of energy and is industrially feasible.

In addition, the second cooling temperature is set at a temperature at which the tar component does not adhere to devices, and the reaction liquid is decompressed after having been cooled to the temperature. Accordingly, the blockage in the decompression valve can be prevented. Furthermore, when the second cooling temperature is a temperature which is a boiling point of water or lower, the volume expansion of water occurring after the reaction liquid has been decompressed can be prevented, and the plant can be stably operated. At this time, the amount of by-products to be produced can be reduced, and accordingly pipes can be prevented from causing a blockage and valves can be prevented from being abraded.

Examples of the present invention will be described below, but the scope of the present invention is not limited to the Examples.

Example 1

An acrolein synthesis experiment was conducted while using an experimental apparatus for a supercritical reaction illustrated in FIG. 2. The experimental conditions are shown in Table 1 (conditions of experiment for evaluating optimal reaction condition).

TABLE 1

Conditions of experiment for evaluating optimal reaction condition

| Name of cases | A-1 | A-2 | A-3 | A-4 | A-5 | B-1 | B-2 | B-3 | B-4 | B-5 |
|---|---|---|---|---|---|---|---|---|---|---|
| Glycerol concentration (% by weight) | 1.5 | 4.5 | 15 | 30 | 40 | 1.5 | 4.5 | 15 | 30 | 40 |
| Proton concentration (mM) | | | 12 | | | 12 | 18 | 36 | 48 | 62 |
| Reaction time (sec) | 15 | 5 | 2 | 0.9 | 0.8 | 15 | 5 | 2 | 0.9 | 0.8 |

In cases A-1 to A-5, the reaction experiment was conducted in which the concentration of sulfuric acid was fixed at 6 mM and the concentration of glycerol was used as a parameter. In addition, in cases B-1 to B-5, the reaction experiment was conducted in which the concentration of sulfuric acid and the reaction time were optimized according to the concentration of the glycerol, on the basis of [Formula 1] and [Formula 2]. The reaction yield obtained in the experiment is illustrated in FIG. 8. In the cases A in which the test conditions are not optimized, the reaction yields are low except the case A-1 in which the concentration of the glycerol is as low as 1.5% by weight. On the other hand, in the cases B in which the reaction time and the concentration of the sulfuric acid were optimized, high reaction yields exceeding 70% were obtained, except the case B-5 in which the concentration of the glycerol exceeded 30% by weight. These results agree with a result in which reaction paths change according to the coordination number of supercritical water in the periphery of glycerol molecules.

From the above described results, it was confirmed that when the concentration of the glycerol was 30% by weight or lower, the reaction yield could be enhanced by optimizing the reaction time and the concentration of sulfuric acid on the basis of [Formula 1] and [Formula 2], and a process could be achieved which showed a high use efficiency of energy and a high raw-material yield.

Example 2

A reaction experiment was conducted under a condition in which the concentration of glycerol was 30% by weight, and an experiment for separating and removing a by-product was conducted. The experimental conditions are shown in Table 2 (conditions of experiment for removing by-product).

TABLE 2

| Conditions of experiment for removing by-product | | | | | | | | | |
|---|---|---|---|---|---|---|---|---|---|
| Name of cases | C-1 | C-2 | C-3 | D-1 | D-2 | D-3 | E-1 | E-2 | E-3 |
| Glycerol concentration (% by weight) | | | | | 30 | | | | |
| Proton concentration (mM) | | | | | 48 | | | | |
| Reaction time (sec) | | | | | 0.9 | | | | |
| Filtration temperature (° C.) | | 10 | | | 200 | | | 250 | |
| Pore diameter of filter (micrometer) | 15 | 40 | 90 | 15 | 40 | 90 | 15 | 40 | 90 |

Figure 9:
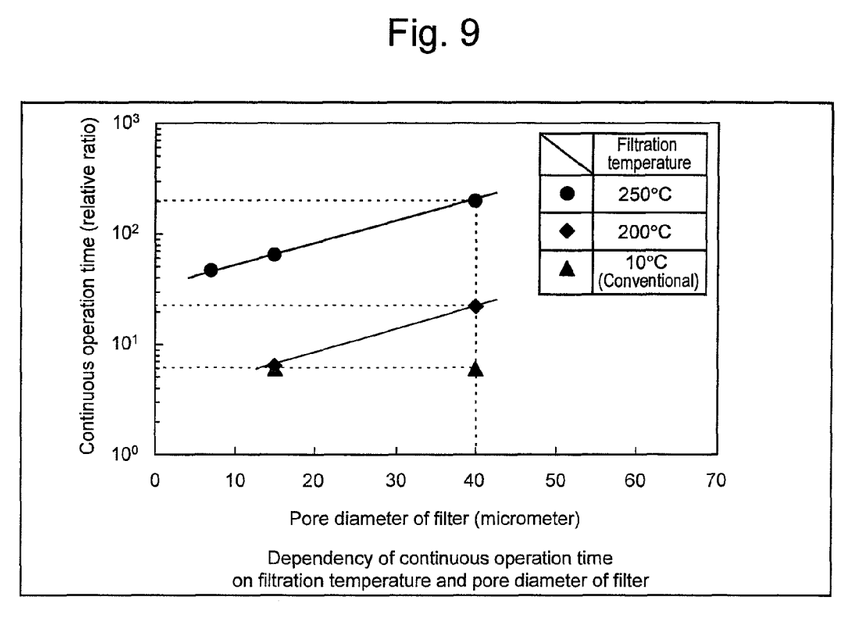
FIG. 9 is a view illustrating the dependency of a continuous operation time on a filtration temperature and a pore diameter of the filter.
Figure 10:
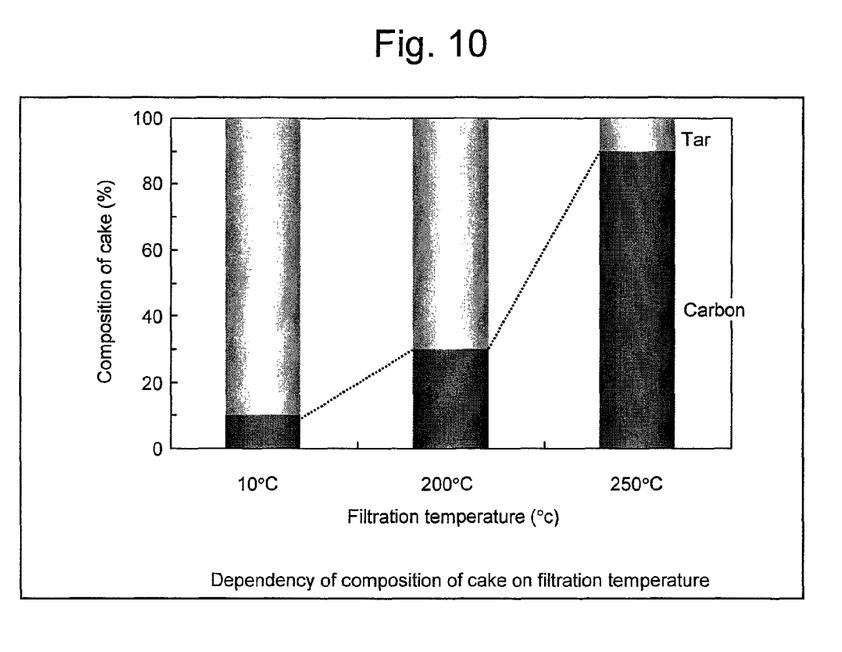
FIG. 10 is a view illustrating the dependency of a composition of a cake on filtration temperature.

Filtration temperatures were set at 10° C., 200° C. and 250° C., and the pore diameters of filters were set at 15 micrometers, 40 micrometers and 60 micrometers. FIG. 9 illustrates an operation time until the differential pressure of the filter reaches 6 MPa which is a withstanding pressure, in this test. In the case in which the pore diameter of the filter was 60 micrometers, the blockage in a decompression valve occurred before the differential pressure of the filter reached the withstanding pressure. Accordingly, the data is not illustrated in the graph. On the other hand, in the case in which the pore diameters of the filter were 15 micrometers and 40 micrometers, the blockage in the decompression valve did not occur, and the reaction experiment could be stably conducted. In addition, the time which was spent before the differential pressure of the filter reached the withstanding pressure could be extended to a 3 times longer period, by changing the pore diameter of the filter from 15 micrometers to 40 micrometers. In addition, the continuous operation time could be extended to a one digit longer period, by raising the filtration temperature from 200° C. to 250° C. The reason is assumed to be because: as the temperature of the filter becomes higher, the viscosity of tar is lowered, the tar more easily passes through the filter, and the tar content in carbon particles decreases; and when the tar content decreases, a force of mutually bonding the carbon particles becomes low, accordingly a layer of accumulated carbon particles in the filter becomes sparse, and the rise of the differential pressure of the filter is remarkably delayed. FIG. 10 illustrates the dependency of a composition of the cake on filtration temperature. Actually, the tar content of the carbon particles which have been removed at 10° C. is 90% by weight, whereas the tar content at 200° C. is 70% by weight and the tar content at 250° C. is 10% by weight, which supports the above described hypothesis. Thus, a process was achieved which could stably operate for a long time while separating and removing by-products such as tar and carbon particles that are produced by the supercritical water reaction.

Example 3

Figure 11:
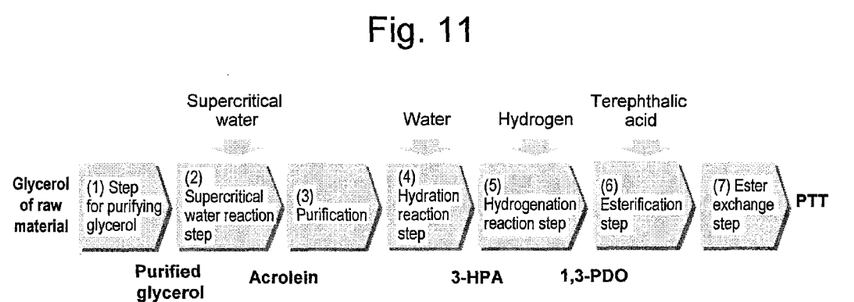
FIG. 11 is a view illustrating a process for obtaining PTT.

FIG. 11 illustrates a process for obtaining polytrimethylene terephthalate (PTT) by synthesizing acrolein from glycerol by using the supercritical water reaction process described in Examples 1 and 2 of the present invention, subjecting the acrolein to a hydration reaction and a hydrogenation reaction to convert the acrolein into 1,3-propanediol, and also condensation-polymerizing the 1,3-propanediol with terephthalic acid. When impurities such as an organic acid (hydrolyzate of oil which is raw material of biodiesel fuel, and the like) and a metal salt (alkaline catalyst for producing biodiesel fuel, and its reactant) are contained in the glycerol of the raw material, the impurities are desirably removed beforehand with a method such as a separating and filtering method, an ion exchange method and a distillation method. This is because the existence of the organic acid causes a decrease of a raw material yield, and the salts precipitate in a supercritical water having a small dielectric constant even though being soluble in water at ordinary temperature and normal pressure, and possibly cause deposition onto pipes and the like. Of course, when the purity of the glycerol is high, the present step can be omitted.

Refined glycerol was converted into acrolein with the supercritical water reaction process described in Examples 1 and 2 of the present invention. The raw material yield obtained at this time was 70.8%. The reaction liquid containing the acrolein is refined by distillation or the like, is then subjected to the hydration reaction in the presence of a catalyst such as a strongly-acidic cation-exchange resin to produce 3-hydroxypropionaldehyde (3-HPA), and then is further subjected to the hydrogenation reaction in the presence of a precious metal catalyst. At this time, a temperature of 50° C., normal pressure and an LHSV value of 0.5/h were selected as conditions of the hydration reaction, and a temperature of 60° C., a pressure of 15 MPa and an LHSV value of 1/h were selected as conditions of the hydrogenation reaction, with reference to Non-Patent Literature 1. As for the yield in each step at this time, the yield of the hydration reaction was 75%, and the yield of the hydrogenation reaction was 95%. Accordingly, the raw material yield in total of the above reactions was approximately 50%. The resultant liquid was distilled and refined, and 1,3-propanediol was obtained.

The obtained 1,3-propanediol and terephthalic acid were subjected to an esterification reaction in the coexistence of a catalyst such as titanium tetrabutoxide, and then the resultant product was subjected to an ester exchange reaction. Thereby, PTT was obtained by polymerization. At this time, a temperature of 210° C., a pressure of 1 atmosphere, a time of 3 h and a molar ratio of 1,3-propanediol and the terephthalic acid of 2.0 were used as conditions of the esterification reaction, and a temperature of 270° C., a pressure of 1 torr and a time of 4 h were used as conditions of the ester exchange reaction. As a result, PTT having the average molecular weight of 20,000 and the b-value of 3 was obtained. Incidentally, the present Example was described as an example for obtaining PTT, but when 1,3-propanediol is obtained as an additive for cosmetics and the like, it is possible to cope with the case by omitting the steps after the esterification reaction. In addition, when obtaining the acrolein and a derivative thereof (acrylic acid or the like), it is possible to cope with the case by omitting the steps after the hydration reaction.

REFERENCE SIGNS LIST

100 . . . Water header
110 . . . High-pressure pump for supercritical water
120 . . . Supercritical water preheater
200 . . . Raw material header
210 . . . High-pressure pump for raw material
220 . . . Raw material preheater
230 . . . Joining point of supercritical water and raw material
310 . . . Reaction pipe heater
400 . . . Cooling water header
410 . . . High-pressure pump for cooling water
420 . . . Joining point of reaction liquid and cooling water
500 . . . Backwashing fluid header
510 . . . Drain
520 . . . Filter
521 . . . Reaction liquid inlet valve of filter
522 . . . Reaction liquid outlet valve of filter
523 . . . Backwashing fluid inlet valve of filter
524 . . . Drain valve of filter
620 . . . Cooler
630 . . . Orifice
640 . . . Pressure control valve
650 . . . Reaction liquid outlet
a . . . a system
b . . . b system

The invention claimed is:

1. A process for synthesis of acrolein by reacting supercritical water and an acid with glycerol, the process comprising: setting a concentration of glycerol in a reaction liquid at 15-30% by weight; also cooling the reaction liquid to 200 to 300° C. in a first cooling; then separating and removing a solid component comprised in the reaction liquid; subsequently cooling the reaction liquid to 60 to 100° C. in a second cooling; and then decompressing the cooled reaction liquid.

2. The process for synthesis according to claim 1, wherein a proton concentration [H$^+$] (% by weight) in the reaction liquid is in a range expressed by the following expression using a glycerol concentration [G] (mM):

$$5 \times \sqrt{[G]} < [H^+] < 20 \times \sqrt{[G]} \qquad \text{[Formula 1]}.$$

3. The process for synthesis according to claim 1, wherein a reaction time t is in a range expressed by the following expression using the glycerol concentration [G] (mM) in the reaction liquid:

$$\frac{3.75}{[G]} < t < \frac{1.5}{[G]}. \qquad \text{[Formula 2]}$$

4. The process for synthesis according to claim 1, wherein a pore diameter of a filter for separating and removing the solid component is 40 micrometers or less.

5. The process for synthesis according to claim 1, wherein the concentration of glycerol is higher than 15% by weight.

6. The process for synthesis according to claim 2, wherein a reaction time t is in a range expressed by the following expression using the glycerol concentration [G] (mM) in the reaction liquid:

$$\frac{3.75}{[G]} < t < \frac{1.5}{[G]}. \qquad \text{[Formula 2]}$$

7. The process for synthesis according to claim 1, wherein the first cooling comprises directly mixing a cooling fluid with the reaction liquid.

8. The process for synthesis according to claim 7, wherein the cooling fluid comprises water.

\* \* \* \* \*